United States Patent
Xu et al.

(10) Patent No.: US 11,435,336 B2
(45) Date of Patent: Sep. 6, 2022

(54) METHOD FOR DETERMINING CONTENT OF LOST GAS IN SHALE GAS CONTENT TEST

(71) Applicants: TSINGHUA UNIVERSITY, Beijing (CN); SHANXI RESEARCH INSTITUTE FOR CLEAN ENERGY, TSINGHUA UNIVERSITY, Shanxi (CN)

(72) Inventors: Ruina Xu, Beijing (CN); Peixue Jiang, Beijing (CN); Kecheng Zeng, Beijing (CN); Fuzhen Zhang, Beijing (CN)

(73) Assignees: TSINGHUA UNIVERSITY, Beijing (CN); SHANXI RESEARCH INSTITUTE FOR CLEAN ENERGY, TSINGHUA UNIVERSITY, Shanxi (CN)

(*) Notice: Subject to any disclaimer, the term of this patent is extended or adjusted under 35 U.S.C. 154(b) by 366 days.

(21) Appl. No.: 16/750,076

(22) Filed: Jan. 23, 2020

(65) Prior Publication Data
US 2020/0240973 A1    Jul. 30, 2020

(30) Foreign Application Priority Data

Jan. 28, 2019 (CN) .......................... 201910081154.0
Dec. 2, 2019 (CN) .......................... 201911212117.5

(51) Int. Cl.
*G01N 33/24* (2006.01)
*E21B 45/00* (2006.01)
(Continued)

(52) U.S. Cl.
CPC .......... *G01N 33/241* (2013.01); *E21B 45/00* (2013.01); *E21B 49/02* (2013.01); *G01N 7/16* (2013.01)

(58) Field of Classification Search
CPC ........ G01N 33/241; G01N 7/16; E21B 45/00; E21B 49/02
See application file for complete search history.

(56) References Cited

U.S. PATENT DOCUMENTS

2009/0260416 A1* 10/2009 Coleman .............. G01N 33/241
73/19.01

FOREIGN PATENT DOCUMENTS

CN              105203428           12/2015

OTHER PUBLICATIONS

Wei Dang "Investigation of gas content of organic-rich shale: A case study from Lower Permian shale in southern North China Basin, central China" (Year: 2018).*

(Continued)

*Primary Examiner* — Catherine T. Rastovski
*Assistant Examiner* — Kaleria Knox
(74) *Attorney, Agent, or Firm* — Brundidge & Stanger, P.C.

(57) ABSTRACT

The present invention discloses a method for determining a content of lost gas in a shale gas content test. The method includes: acquiring a shale core and recording the time required for acquiring the shale core; carrying out a desorption experiment on the shale core to obtain desorption data; acquiring a fitting objective function; fitting the desorption data by using the fitting objective function to obtain fitted desorption data; determining fitting parameters according to the desorption data and the fitted desorption data; correcting the time required for acquiring the shale core according to the fitting parameters; and obtaining the content of lost gas according to the fitting parameters and the corrected time required for acquiring the shale core. The present invention can improve the determining precision of the content of the lost gas.

11 Claims, 1 Drawing Sheet

(51) Int. Cl.
    *E21B 49/02* (2006.01)
    *G01N 7/16* (2006.01)

(56) References Cited

OTHER PUBLICATIONS

Weisstein "Least Squares Fitting". (Year: 1999).*

* cited by examiner

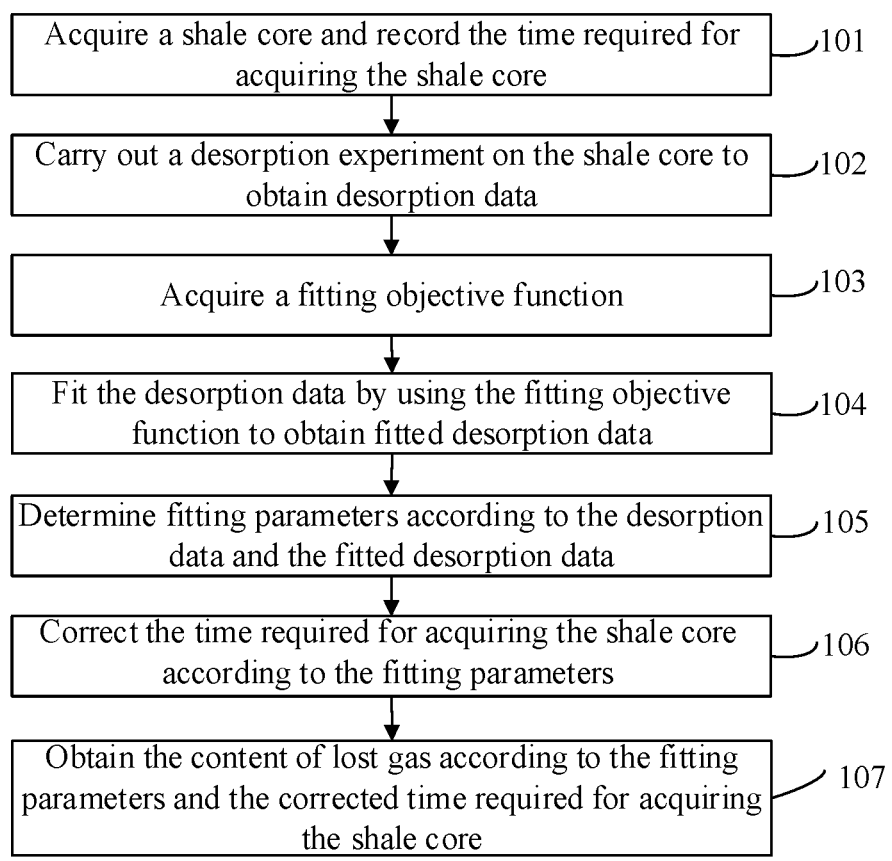

METHOD FOR DETERMINING CONTENT OF LOST GAS IN SHALE GAS CONTENT TEST

CROSS-REFERENCE TO RELATED APPLICATIONS

This application claims priority to Chinese Patent Application No. 201910081154.0, filed on Jan. 28, 2019, and Chinese Patent Application No. 201911212117.5, filed on Dec. 2, 2019, the entire contents of which are incorporated herein by reference.

TECHNICAL FIELD

The present invention relates to the technical field of shale gas content estimation, and in particular, to a method for determining a content of lost gas in a shale gas content test.

BACKGROUND

With the adjustment of the world energy structure, natural gas, as a clean energy, plays an increasingly important role. Shale gas is a kind of unconventional natural gas, with huge reserves and mature commercial exploitation in the United States. China also regards shale gas exploitation as its national strategy.

Before shale gas exploitation, shale gas reservoirs and the content of shale gas in the formation need to be tested and selected, to find economically valuable blocks for exploitation. There are many direct and indirect methods for evaluating the content of shale gas in the formation. The direct method is a desorption method. A core of a target formation is obtained through a drill bit and lifted from underground to the surface. During this process, some gas is lost, which is called lost gas. After the core is obtained, the formation temperature is simulated on the surface, and a desorption experiment on the core is carried out to measure the content of desorbed gas in the core. On this basis, the content of lost gas in the drill string lifting process is estimated in combination with a lost gas estimation model, and the total gas content in the reservoir is obtained by summation. The indirect methods include an isothermal adsorption method, a logging interpretation method and a statistical analysis method. The isothermal adsorption method is based on isothermal adsorption experiments. The drilled core is subjected to saturation isothermal adsorption experiments, and the measured gas content is the maximum gas content of the reservoir. According to the logging interpretation method, the gas content of the reservoir is obtained by inversion calculation through response signals such as rays and acoustic waves. The statistical analysis method is based on matching tests of several geological parameters, and main control factors are selected according to a statistical model to fit and estimate the gas content of the reservoir. According to the indirect methods, more reservoir information can be obtained, but the direct method is still the most widely used in gas content estimation, and its estimation accuracy is the highest.

In the process of estimating core gas content by the direct method, the total gas content is subdivide into lost gas, desorbed gas and residual gas. The lost gas refers to the gas escaping from the core when the core is taken from underground to the surface. It is difficult to measure the content of the lost gas which is often estimated through the content of the desorbed gas. The desorbed gas refers to the gas of which the content is measured by taking the core from the surface and putting the core into a desorption canister to carry out a desorption experiment under a formation temperature environment. The residual gas refers to the gas remaining in the core that cannot be measured after the desorption experiment is completed. The gas accounts for a relatively small proportion and can often be ignored, but it can also be measured by breaking the core to release the residual gas through the crushing experiment.

At present, the method for estimating the lost gas of shale gas is mainly developed from a method for determining lost gas of coalbed methane, but there is a huge difference between the shale gas and the coalbed methane. Due to the shallow burial of the coalbed methane, the coring speed is faster and the gas escape is less. Moreover, the large content of organic matter in the coal core leads to a large proportion of adsorbed gas in the coalbed methane and a slow loss rate of the coalbed methane. Therefore, in the coring process, the proportion of the lost gas in the coalbed methane is much smaller than that in the shale gas. Due to the huge proportion of the lost gas, the method for estimating the lost gas in the shale gas cannot be used directly to estimate the lost gas in the coalbed methane. In this context, a more accurate method for estimating lost gas in shale that is more in line with the engineering practice is needed.

SUMMARY

An objective of the present invention is to provide a method for determining a content of lost gas in a shale gas content test, which can improve the determining precision of the content of the lost gas.

To achieve the above objective, the present invention provides the following technical solution.

A method for determining a content of lost gas in a shale gas content test, including:

acquiring a shale core and recording the time required for acquiring the shale core;

carrying out a desorption experiment on the shale core to obtain desorption data;

acquiring a fitting objective function;

fitting the desorption data by using the fitting objective function to obtain fitted desorption data;

determining fitting parameters according to the desorption data and the fitted desorption data;

correcting the time required for acquiring the shale core according to the fitting parameters; and obtaining the content of lost gas according to the fitting parameters and the corrected time required for acquiring the shale core.

Optionally, the carrying out a desorption experiment on the shale core to obtain desorption data includes:

putting the shale core into a desorption canister and discharging air in a dead volume of the desorption canister;

sealing the desorption canister;

heating the sealed desorption canister to a set temperature;

acquiring gas output of the desorption canister every set time and recording current acquisition time until the gas output of the desorption canister is stable; and obtaining desorption data accord to the gas output of the desorption canister and the corresponding acquisition time.

Optionally, after the step of carrying out a desorption experiment on the shale core to obtain desorption data, before the step of acquiring a fitting objective function, the method further includes:

preprocessing the acquisition time in the desorption data, so that a difference between adjacent acquisition time is the set time.

Optionally, the fitting objective function is:

$$Q = \frac{4\pi k}{D} \sum_{n=1}^{\infty} \frac{\exp(-D\alpha_n^2 t) - \exp(-D\alpha_n^2 t_0)}{\alpha_n^4} -$$

$$\frac{2\pi k R}{D} \sum_{n=1}^{\infty} \frac{\exp[-D\alpha_n^2(t-t_0)]J_2(R\alpha_n)}{\alpha_n^3 J_1(R\alpha_n)} + \frac{k\pi R^4}{8D}$$

where k is a depressurization rate in the process of acquiring the shale core, D is a diffusion rate of gas in the porous medium core, R is a core radius, $t_0$ is the time required for acquiring the shale core, $\alpha_n$ is a characteristic value, Q is an accumulated flow, and t is duration of a desorption experiment.

Optionally, the determining fitting parameters according to the desorption data and the fitted desorption data includes:
determining fitting parameters by using formula $$\min \sum_{n=1}^{N} [Q(t_n) - Q_n]^2,$$

where the fitting parameters include the depressurization rate k in the process of acquiring a shale core and the diffusion rate D of gas in the porous medium core, where $Q(t_n)$ is the fitted desorption data, $Q_n$ is the desorption data, and N is the number of the desorption data.

Optionally, the time required for acquiring the shale core is corrected by using formula $$\bar{t}_0 = \frac{kt_0 + p_0}{p_w} t_0,$$

where $\bar{t}_o$ is the corrected time required for acquiring the shale core, k is a depressurization rate in the process of acquiring the shale core, $p_0$ is the local atmospheric pressure, $p_w$ is the mud water column pressure, and $t_0$ is the time required for acquiring the shale core.

Optionally, the obtaining the content of lost gas according to the fitting parameters and the corrected time required for acquiring the shale core includes:
calculating the content of lost gas by using formula $$Q_{Lost} = \pi R^2 k \bar{t}_0 - \frac{\pi k R^4}{8D} + \frac{4\pi k}{D} \sum_{n=1}^{\infty} \frac{\exp(-D\alpha_n^2 \bar{t}_0)}{\alpha_n^4},$$

where k is a depressurization rate in the process of acquiring the shale core, D is a diffusion rate of gas in the porous medium core, R is a core radius, $\bar{t}_o$ is the corrected time required for acquiring the shale core, $\alpha_n$ is a characteristic value, and $Q_{lost}$ is the lost gas volume.

Optionally, the desorption data is fitted by using a least square method to obtain fitted desorption data.

Optionally, the set time is 5 min.

Optionally, the set temperature is 70° C.

According to specific embodiments provided in the present invention, the present invention discloses the following technical effects.

According to the present invention, the desorption data is subjected to non-linear fitting by adopting the fitting objective function, and the least square method is adopted for the fitting process. The fitting precision is higher, physical conditions of the actual coring process are met better, and the calculation result of the content of lost gas is more accurate.

BRIEF DESCRIPTION OF THE DRAWINGS

To describe the technical solutions in the embodiments of the present invention or in the prior art more clearly, the following briefly introduces the accompanying drawings required for describing the embodiments. Apparently, the accompanying drawings in the following description show merely some embodiments of the present invention, and a person of ordinary skill in the art may still derive other drawings from these accompanying drawings without creative efforts.

FIG. 1 is a flow chart of a method for determining a content of lost gas in a shale gas content test according to the present invention.

DETAILED DESCRIPTION

The following clearly and completely describes the technical solutions in the embodiments of the present invention with reference to accompanying drawings in the embodiments of the present invention. Apparently, the described embodiments are merely some rather than all of the embodiments of the present invention. All other embodiments obtained by a person of ordinary skill in the art based on the embodiments of the present invention without creative efforts shall fall within the protection scope of the present invention.

An objective of the present invention is to provide a method for determining a content of lost gas in a shale gas content test, which can improve the determining precision of the content of the lost gas.

In order that the foregoing objectives, features, and advantages of the present invention can be more clearly understood, the present invention will be further described in detail with reference to the accompanying drawings and specific embodiments.

FIG. 1 is a flow chart of a method for determining a content of lost gas in a shale gas content test according to the present invention. As shown in FIG. 1, a method for determining a content of lost gas in a shale gas content test includes:

Step 101: Acquire a shale core and record the time required for acquiring the shale core.

Step 102: Carry out a desorption experiment on the shale core to obtain desorption data.

Step 103: Acquire a fitting objective function.

Step 104: Fit the desorption data by using the fitting objective function to obtain fitted desorption data.

Step 105: Determine fitting parameters according to the desorption data and the fitted desorption data.

Step 106: Correct the time required for acquiring the shale core according to the fitting parameters.

Step 107: Obtain the content of lost gas according to the fitting parameters and the corrected time required for acquiring the shale core.

Specifically, in step 101, the shale core is obtained through a drilled well, and the time required for acquiring the shale core is also the drill string lifting time.

In step 102, the shale core is put into a desorption canister after mud on the surface of the shale core is wiped off. Since the volume $V_{canister}$ of the desorption canister is greater than the volume $V_{core}$ of the shale core, there is a dead volume in the desorption canister. It is necessary to exhaust air in the dead volume before the desorbed gas test can be carried out. Therefore, the desorption canister is filled with fine sand to exhaust the air in the dead volume in the desorption canister, and the desorption canister is closed for sealing. After the desorption canister is heated to 70° C. (formation temperature) and the temperature is stable, an air outlet valve installed on the desorption canister is switched on, and gas output of desorbed gas is measured by means of a flow meter. The reading of the flow meter is acquired once every 5 min for the desorption experiment, and the current acquisition time is recorded. The desorption duration of desorbed gas is 20-50 h. Whether desorption is completed can be determined according to whether the readings of the flow meter are stable within a certain period of time. After desorption is stable, desorption section experimental data $\{(t_n, Q_n)|(n=1, 2, \ldots, N)\}$ is obtained through desorption experiments, where $t_n$ denotes time series, and $Q_n$ denotes total flow data series of the desorbed gas corresponding to the time series $t_n$ respectively.

Then the desorption data $\{(t_n, Q_n)|(n=1, 2, \ldots, N)\}$ is preprocessed. Due to the limitation of drilling site conditions, power supply cannot be guaranteed at any time. Desorption experiments cannot be carried out under the condition of power failure, and thus the obtained desorption data is not necessarily uniformly distributed in the recorded time series. Therefore, a breakpoint of the time series is processed, and the power outage time length is deducted, so that the time series is reprocessed for uniform distribution. The processed time series meets $t_n-t_{n-1}=5$ min, so that the desorption data is uniformly distributed and conforms to a desorption section model, which facilitates data fitting.

After the shale core desorption experiment is completed, a crushing experiment can be adopted. The shale core is taken out of the desorption canister and put into a crushing device. After the desorption canister is sealed, a crushing switch is turned on to crush the shale core and acquire residual gas. The residual gas content $Q_{residue}$ is recorded and used for determining the gas content of the shale core.

The fitting objective function in step 103 is as follows:

$$Q = \frac{4\pi k}{D} \sum_{n=1}^{\infty} \frac{\exp(-D\alpha_n^2 t) - \exp(-D\alpha_n^2 t_0)}{\alpha_n^4} -$$

$$\frac{2\pi k R}{D} \sum_{n=1}^{\infty} \frac{\exp[-D\alpha_n^2(t-t_0)]J_2(R\alpha_n)}{\alpha_n^3 J_1(R\alpha_n)} + \frac{k\pi R^4}{8D}$$

where k is a depressurization rate in the process of acquiring the shale core, D is a diffusion rate of gas in the porous medium core, R is a core radius, $t_0$ is the drill string lifting time, $\alpha_n$ is a characteristic value, Q is an accumulated flow, and t is desorption time. It is analyzed according to the convergence of series summation that the foregoing summation form is stable convergence. On the premise of meeting the existing computer precision, summation results of first 50 items can be used to characterize an objective function within the precision range.

The fitting method used in step 104 is a least square method.

In step 105, parameter values in the objective function through the given experimental data sequence $\{(t_n, Q_n)|(n=1, 2, \ldots, N)\}$ of desorbed gas with reference to the fitting objective function, so that the sum of squared differences between the desorption data and the fitted desorption data is minimized. The specific data processing formula is shown below:

$$\min \sum_{n=1}^{N} [Q(t_n) - Q_n]^2$$

where $Q(t_n)$ is a value of the time series substituted into the objective function, namely the fitted desorption data; $Q_n$ is a desorption experimental data value corresponding to the time series, namely the desorption data. The parameters D and k in the objective function are obtained by solving the optimization problem.

Strictly, for the correction process in step 106, the drill string lifting time starts from the time when the shale pore pressure and the mud water column pressure are balanced. The relationship between the mud water column pressure and the drill string lifting time is calculated in combination with the drilling depth, the shale pore pressure is calculated by fitting the obtained parameter k. As a result, the time when the shale pore pressure and the mud water column pressure are balanced is calculated, thereby obtaining corrected drill string lifting time data $\bar{t}_o$.

$$\bar{t}_0 = \frac{kt_0 + p_0}{p_w} t_0$$

$\bar{t}_o$ is the corrected time required for acquiring the shale core, k is a depressurization rate in the process of acquiring the shale core, $t_0$ is the time required for acquiring the shale core. $p_0$ is the local atmospheric pressure, and $p_w$ is the mud water column pressure. When the data error is large, $\bar{t}_0=0.5t_0$ can be used as the corrected drill string lifting time data.

In step 107, the obtained parameters D and k and the time $\bar{t}_o$ required for acquiring the shale core are substituted into the following objective function:

$$Q_{Lost} = \pi R^2 k \bar{t}_0 - \frac{\pi k R^4}{8D} + \frac{4\pi k}{D} \sum_{n=1}^{\infty} \frac{\exp(-D\alpha_n^2 \bar{t}_0)}{\alpha_n^4}$$

where k is a depressurization rate in the process of acquiring the shale core, D is a diffusion rate of gas in the porous medium core, R is a core radius, $\bar{t}_o$ is the corrected drill string lifting time, $\alpha_n$ is a characteristic value, and $Q_{lost}$ is the lost gas volume.

Specifically, the estimated content $Q_{Lost}$ of lost gas, experimental data $Q_N$ of the content of desorbed gas, and experimental data $Q_{residue}$ of the content of residual gas are added to obtain the shale gas content based on a segmented estimation method. The formula is as follows:

$Q_{total}=Q_{Lost}+Q_N+Q_{residue}.$

The present invention also discloses the following technical effects:

1. Compared with the method for estimating the content of lost gas through a straight line method in the prior art, the method for determining the content of lost gas provided by the present invention is also based on desorption experimental data, but nonlinear fitting is carried out, and the fitting precision is higher.

2. According to the present invention, the pore pressure of the shale reservoir can be obtained by fitting according to the fitting objective function, and then the corrected shale core drill string lifting time $\bar{t}_o$ can be calculated according to the mud water column pressure. Compared with the fixed parameters in the prior art, the method for calculating the drill string lifting time provided by the patent is more accurate, and is suitable for different reservoirs and different coring conditions.

3. According to the present invention, the relationship between the lost gas volume and time in the shale coring process and the relationship between the desorbed gas volume and time in the desorption experiment are distinguished and fitted segmentally. Compared with the mode of unified treatment of the two in the prior art, the method provided by the present invention is more suitable for actual engineering conditions and more formation conditions (including pore pressure and gas content) can be obtained by fitting.

Each embodiment of the present specification is described in a progressive manner, each embodiment focuses on the difference from other embodiments, and the same and similar parts between the embodiments may refer to each other.

Several examples are used herein for illustration of the principles and embodiments of the present invention. The description of the embodiments is used to help illustrate the method and its core principles of the present invention. In addition, a person of ordinary skill in the art can make various modifications in terms of specific embodiments and scope of application in accordance with the idea of the present invention. In conclusion, the content of the present specification shall not be construed as a limitation to the present invention.

What is claimed is:

1. A method for determining a content of lost gas in a shale gas content test, comprising:
   acquiring a shale core and recording time required for acquiring the shale core;
   carrying out a desorption experiment on the shale core to obtain desorption data;
   acquiring a fitting objective function;
   fitting the desorption data by using the fitting objective function to obtain fitted desorption data;
   determining fitting parameters according to the desorption data and the fitted desorption data;
   correcting the time required for acquiring the shale core according to the fitting parameters; and
   obtaining the content of lost gas according to the fitting parameters and the corrected time required for acquiring the shale core,
   wherein the time required for acquiring the shale core is corrected by using formula $$\bar{t}_0 = \frac{kt_0 + p_0}{p_w} t_0,$$

wherein $\bar{t}_0$ is the corrected time required for acquiring the shale core, k is a depressurization rate in the process of acquiring the shale core, $p_0$ is a local atmospheric pressure, $p_w$ is a mud water column pressure, and $t_0$ is the time required for acquiring the shale core.

2. The method for determining a content of lost gas in a shale gas content test according to claim 1, wherein the carrying out a desorption experiment on the shale core to obtain desorption data comprises:
   putting the shale core into a desorption canister and discharging air in a dead volume of the desorption canister;
   sealing the desorption canister;
   heating the sealed desorption canister to a set temperature;
   acquiring gas output of the desorption canister every set time and recording current acquisition time until the gas output of the desorption canister is stable; and
   obtaining desorption data accord to the gas output of the desorption canister and the corresponding acquisition time.

3. The method for determining a content of lost gas in a shale gas content test according to claim 2, wherein after the step of carrying out a desorption experiment on the shale core to obtain desorption data, before the step of acquiring a fitting objective function, the method further comprises:
   preprocessing the acquisition time in the desorption data, so that a difference between adjacent acquisition time is the set time.

4. The method for determining a content of lost gas in a shale gas content test according to claim 1, wherein, the fitting objective function is:

$$Q = \frac{4\pi k}{D} \sum_{n=1}^{\infty} \frac{\exp(-D\alpha_n^2 t) - \exp(-D\alpha_n^2 t_0)}{\alpha_n^4} - \frac{2\pi k R}{D} \sum_{n=1}^{\infty} \frac{\exp[-D\alpha_n^2(t-t_0)]J_2(R\alpha_n)}{\alpha_n^3 J_1(R\alpha_n)} + \frac{k\pi R^4}{8D}$$

wherein k is a depressurization rate in the process of acquiring the shale core, D is a diffusion rate of gas in the porous medium core, R is a core radius, $t_0$ is the time required for acquiring the shale core, $\alpha_n$ is a characteristic value, Q is an accumulated flow, and t is duration of a desorption experiment.

5. The method for determining a content of lost gas in a shale gas content test according to claim 1, wherein the determining fitting parameters according to the desorption data and the fitted desorption data comprises:
   determining fitting parameters by using formula $$\min \sum_{n=1}^{N} [Q(t_n) - Q_n]^2,$$

wherein the fitting parameters comprise the depressurization rate k in the process of acquiring a shale core and the diffusion rate D of gas in the porous medium core, wherein $Q(t_n)$ is the fitted desorption data, $Q_n$ is the desorption data, and N is the number of the desorption data.

6. The method for determining a content of lost gas in a shale gas content test according to claim 1, wherein the obtaining the content of lost gas according to the fitting parameters and the corrected time required for acquiring the shale core comprises:

calculating the content of lost gas by using formula $$Q_{Lost} = \pi R^2 k \bar{t}_0 - \frac{\pi k R^4}{8D} + \frac{4\pi k}{D} \sum_{n=1}^{\infty} \frac{\exp(-D\alpha_n^2 \bar{t}_0)}{\alpha_n^4},$$

wherein k is a depressurization rate in the process of acquiring the shale core, D is a diffusion rate of gas in the porous medium core, R is a core radius, $\bar{t}_0$ is the corrected time required for acquiring the shale core, $\alpha_n$ is a characteristic value, and $Q_{lost}$ is the lost gas volume.

7. The method for determining a content of lost gas in a shale gas content test according to claim 1, wherein the desorption data is fitted by using a least square method to obtain fitted desorption data.

8. The method for determining a content of lost gas in a shale gas content test according to claim 2, wherein the set time is 5 min.

9. The method for determining a content of lost gas in a shale gas content test according to claim 2, wherein the set temperature is 70° C.

10. The method for determining a content of lost gas in a shale gas content test according to claim 4, wherein the determining fitting parameters according to the desorption data and the fitted desorption data comprises:

determining fitting parameters by using formula $$\min \sum_{n=1}^{N} [Q(t_n) - Q_n]^2,$$

wherein the fitting parameters comprise the depressurization rate k in the process of acquiring a shale core and the diffusion rate D of gas in the porous medium core, wherein $Q(t_n)$ is the fitted desorption data, $Q_n$ is the desorption data, and N is the number of the desorption data.

11. The method for determining a content of lost gas in a shale gas content test according to claim 3, wherein the set time is 5 min.

* * * * *